United States Patent [19]

Fritsch et al.

[11] 4,118,429
[45] Oct. 3, 1978

[54] PRODUCTION AND RECOVERY OF PARA-XYLENE

[75] Inventors: Thomas R. Fritsch, Lombard; Mark C. Anderson, Palatine, both of Ill.

[73] Assignee: UOP Inc., Des Plaines, Ill.

[21] Appl. No.: 836,273

[22] Filed: Sep. 26, 1977

[51] Int. Cl.² .......................... C07C 7/13; C07C 5/22
[52] U.S. Cl. .............................. 260/674 SA; 208/143; 208/310 Z; 260/668 A; 260/674 A
[58] Field of Search ........ 260/674 SA, 674 A, 668 A; 208/143, 310 Z

[56] References Cited

U.S. PATENT DOCUMENTS

| | | | |
|---|---|---|---|
| 3,201,344 | 8/1965 | Broughton | 208/143 |
| 3,239,455 | 3/1966 | Lickus et al. | 208/143 |
| 3,636,121 | 1/1972 | Stine et al. | 260/674 SA |
| 3,700,744 | 10/1972 | Berger et al. | 260/668 A |
| 3,707,550 | 12/1972 | Stine et al. | 260/674 SA |

Primary Examiner—Delbert E. Gantz
Assistant Examiner—C. E. Spresser
Attorney, Agent, or Firm—James R. Hoatson, Jr.; Robert W. Erickson; William H. Page, II

[57] ABSTRACT

A $C_8$-aromatic hydrocarbon mixture containing para-xylene is subjected to adsorption-separation in contact with a crystalline aluminosilicate adsorbent which selectively retains para-xylene. Raffinate therefrom, being a para-xylene deficient $C_8$-aromatic concentrate, is isomerized in contact with a catalytic composite containing a Group VIII noble metal component to form additional para-xylene. Isomerization conditions employed to produce the para-xylene, also effect the formation of olefinic material. To prevent the adverse effect which olefins exhibit toward the efficiency and capacity of the zeolitic adsorbent, the isomerization effluent is subjected to hydrotreating at conditions which provide a liquid-phase operation and saturate olefins without saturation of the $C_8$-aromatics. The hydrotreating is effected in contact with a substantially non-acidic catalytic composite comprising a Group VIII noble metal component.

10 Claims, 1 Drawing Figure

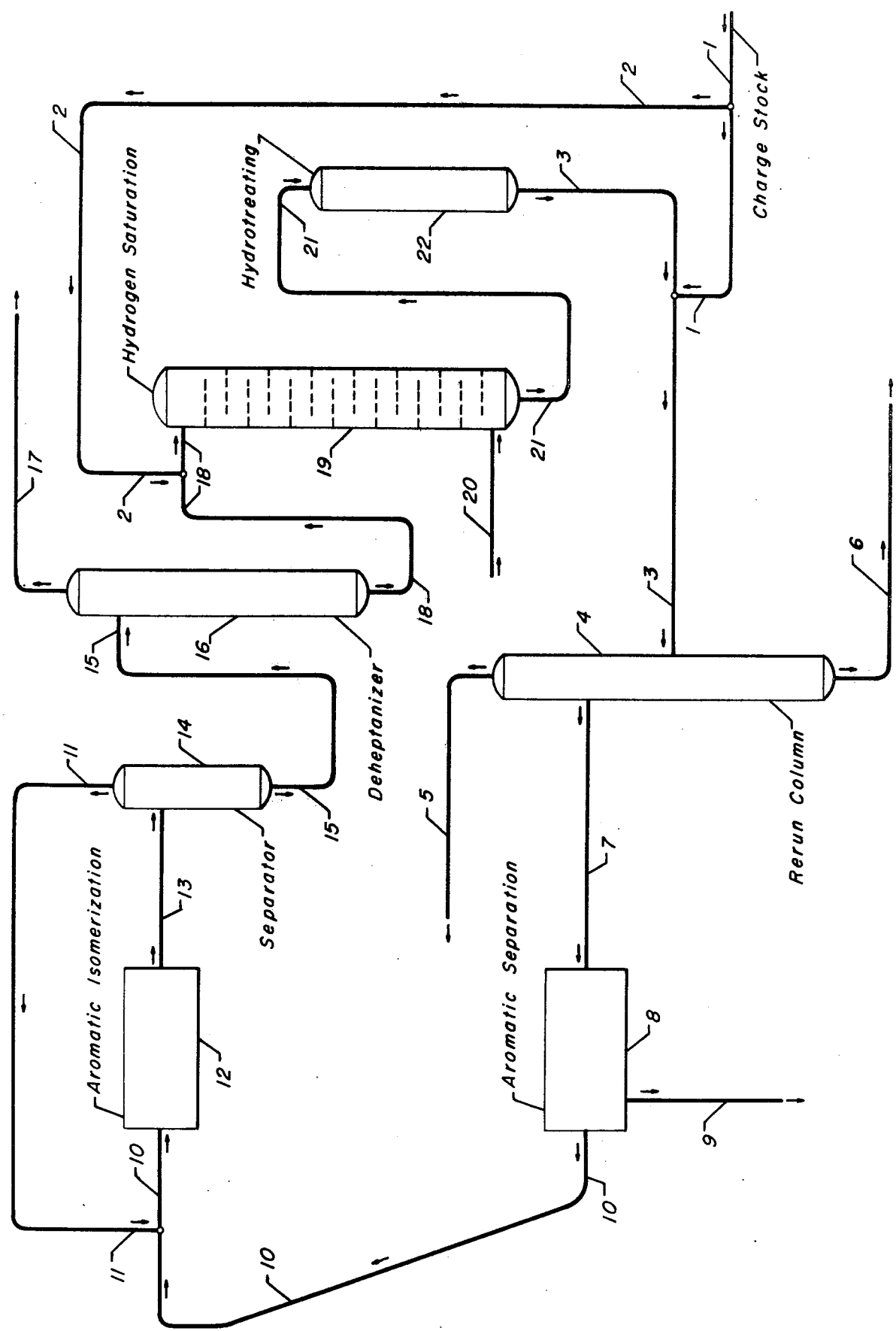

PRODUCTION AND RECOVERY OF PARA-XYLENE

APPLICABILITY OF INVENTION

As herein described, the process encompassed by our inventive concept is directed toward the production and recovery of aromatic hydrocarbons. More specifically, the present invention is intended for utilization in the production of particular bi-alkyl substituted aromatic hydrocarbons having isomeric counterparts. One class of such compounds is the $C_8$-aromatics, ortho-xylene, meta-xylene and para-xylene, a mixture of which generally includes ethylbenzene. Another class is the $C_{10}$-aromatics, ortho-cymene, meta-cymene and para-cymene. Of these, the para isomers currently appear to be in the shortest supply and the greatest demand. Principle uses of para-xylene include the synthesis of terephthalic acid for production of synthetic resins and fibers, and in vitamin and other pharmaceutical syntheses. Para-cymene is employed primarily for the production of para-cresol. Further description of our invention will be limited to the production and recovery of para-xylene.

Regardless of the method by which para-xylene is produced — catalytic condensation, isomerization — the product effluent is an equilibrium mixture of ortho-xylene, meta-xylene, para-xylene and ethylbenzene. Generally, the proportions approximate 50.0% meta-xylene, 20.0% para-xylene, 20.0% ortho-xylene and 10.0% ethylbenzene. The present invention is intended to be applicable to the recovery of the para-xylene contained in such mixtures, and the production thereof via isomerization of the other components. The charge stock to the present process may be a substantially pure $C_8$-aromatic concentrate, or a mixture thereof with other classes of hydrocarbons such as naphthenes, paraffins, other aromatics, etc. $C_8$-aromatics are also obtained in the effluent from various petroleum conversion processes such as catalytic cracking, catalytic reforming, naphtha pyrolysis to produce ethylene, etc. It is understood that the particular charge stock, or source of the $C_8$-aromatic concentrate is not a limitation upon the scope of our invention.

Briefly, a mixture of $C_8$-aromatic hydrocarbons is subjected to absorption-separation in contact with a crystalline aluminosilicate adsorbent which selectively retains therein the para-xylene which is removed and recovered therefrom through the use of a suitable desorbent. The rejected xylene isomers and ethylbenzene are isomerized in contact with an acid-acting catalytic composite comprising a Group VIII noble metal component. We have found that at the conditions necessary to effect isomerization reactions to form additional para-xylene, olefinic hydrocarbons are produced in relatively minor quantities. Those skilled in the art of adsorption-separation via contact with crystalline aluminosilicate molecular sieves are well aware of the detrimental effect exhibited by even minor amounts of olefinic hydrocarbons upon the capacity and efficiency of the zeolitic molecular sieve to adsorb the desired component of the mixture. As hereinafter indicated, this awareness is evidenced by prior art which utilizes a hydrotreating zone in the pretreatment of the fresh feed charge stock; however, such pretreatment is effected with the intent to saturate olefins and aromatics, as well as reducing both sulfur and nitrogen concentrations. In accordance with our invention, the hydrotreating technique constitutes a low-severity, liquid-phase operation effected at conditions which saturate the olefins without substantial saturation of aromatic hydrocarbons.

OBJECTS AND EMBODIMENTS

A principal object of our invention is to provide a more efficient process for the production and recovery of para-xylene. A corollary objective is to enhance the efficiency and capacity of a crystalline aluminosilicate absorbent employed in the adsorption-separation of para-xylene from its isomers and ethylbenzene.

More specifically, it is an object to improve a combination aromatic isomerization/adsorption-separation process for the production and recovery of para-xylene from a mixture of $C_8$-aromatic hydrocarbons.

In one embodiment, therefore, our invention directs itself toward a process for the production and recovery of para-xylene from a mixture of $C_8$-aromatic hydrocarbons, which process comprises the sequential steps of: (a) contacting said mixture with a crystalline aluminosilicate adsorbent, in an adsorption-separation zone, at conditions selected to effect the selective retention therein of para-xylene; (b) withdrawing a para-xylene deficient $C_8$-aromatic raffinate stream from said adsorption-separation zone and contacting said adsorbent with a desorbent to effect removal and recovery of para-xylene therefrom; (c) introducing said raffinate stream into an aromatic isomerization reaction zone maintained at isomerization conditions which convert $C_8$-aromatic hydrocarbons into para-xylene and which effect the production of olefinic hydrocarbons; (d) hydrotreating the resulting isomerization reaction zone effluent, in a hydrotreating zone, at hydrotreating conditions selected to (i) provide a liquid-phase operation and (ii) saturate said olefinic hydrocarbons without substantial saturation of $C_8$-aromatic hydrocarbons; and, (e) introducing at least a portion of the resulting olefin-free reaction zone effluent into said adsorption-separation zone to recover additional para-xylene.

Other objects and embodiments will become evident, to those possessing the requisite degree of skill in the appropriate art, from the following more detailed discussion. In one such other embodiment, the $C_8$-aromatic hydrocarbon fresh feed mixture is combined with the olefin-free hydrotreating effluent, and introduced therewith into the molecular sieve adsorption-separation zone. Another embodiment involves introducing the $C_8$-aromatic charge stock into the hydrotreating zone in admixture with the isomerization zone effluent.

CITATION OF RELEVANT PRIOR ART

As hereinbefore stated, our inventive concept encompasses the known combination process of (1) producing para-xylene via the catalytic isomerization of $C_8$-aromatic hydrocarbon mixtures and, (2) the recovery thereof by way of selective adsorptive-separation utilizing a zeolitic, crystalline aluminosilicate molecular sieve. In essence, a liquid-phase, catalytic hydrotreating reaction zone is interposed between the isomerization section and the adsorptive-separation section. This serves to eliminate olefinic hydrocarbons, formed during the aromatic isomerization reaction, via hydrogenation to paraffinic counterparts which are innocuous with respect to the selected crystalline aluminosilicate adsorbent employed in the adsorptive-separation section. Through this technique, the capacity and efficiency of the zeolitic molecular sieve is significantly improved.

It is recognized and acknowledged that many illustrations of aromatic isomerization processing techniques are to be found in the prior art; likewise, zeolitic molecular sieve adsorption/separation has been shown to be applicable to many classes of hydrocarbons. Since the process encompassed by the present invention involves isomerization of $C_8$-aromatic hydrocarbons in combination with molecular sieve adsorption/separation to recover the desired isomer (para-xylene), which combination has an intermediate hydrotreating zone, it is believed that the most relevant prior art will be directed toward (1) combinations of isomerization and zeolitic adsorption/separation, and, (2) hydrotreating in combination with the separation of classes of hydrocarbons by way of crystalline aluminosilicate adsorption. Copies of the prior art hereinbelow delineated accompany this application.

U.S. Pat. No. 3,636,121 (Cl. 260-674A) issued Jan. 18, 1972, directs itself toward a dual adsorption and isomerization process utilizing first and second molecular sieve adsorption zones. The first adsorption zone effects separation of the fresh feed stream (a $C_8$-aromatic concentrate) into (1) a para-xylene/ethylbenzene concentrate and, (2) an ortho-xylene/meta-xylene concentrate. The latter stream is subjected to isomerization, to produce additional para-xylene/ethylbenzene, the effluent from which is passed into the first adsorption zone. The para-xylene/ethylbenzene concentrate therefrom is introduced into the second molecular sieve separation zone from which the para-xylene and ethylbenzene are recovered as individual streams. Nowhere is there recognition of the deleterious effects of olefinic hydrocarbons, produced in minor quantities in the isomerization reaction zone, upon the efficiency and capacity of the zeolitic molecular sieve adsorbent. Furthermore, the teachings do not contemplate a low severity, liquid-phase hydrotreatment for the purpose of rendering these olefinic hydrocarbons innocuous.

U.S. Pat. No. 3,700,744 (Cl. 260-668A), issued Oct. 24, 1972, discloses a combination process of aromatic isomerization/adsorptive-separation similar to the foregoing. The $C_8$-aromatic charge stock is first fractionally distilled to produce (1) an ortho-xylene free fraction of ethylbenzene, meta-xylene and para-xylene, and, (2) a relatively ortho-xylene and ethylbenzene free fraction of meta-xylene and para-xylene. The former is subjected to isomerization, the effluent from which is introduced into the fractional distillation zone; the latter meta-xylene/para-xylene fraction is separated in the adsorptive separation zone. Hydrotreating of the isomerization reaction zone effluent is not disclosed in this combination process.

U.S. Pat. No. 3,707,550 (Cl. 260-674SA), issued Dec. 26, 1972, initially subjects the fresh feed charge stock to fractionation for the recovery of ortho-xylene in a $C_9$-aromatic concentrate. The remainder of the combination process essentially follows the procedures of U.S. Pat. No. 3,636,121 above described.

U.S. Pat. No. 3,201,344 (Cl. 208-143), issued Aug. 17, 1965, is specifically directed toward a combination process for refining hydrocarbon lubricating oils. Absorption-separation is effected utilizing a 13X or 10X molecular sieve to reject, as the raffinate stream, branched chain hydrocarbons, polynuclear cyclics and polyalkyl-substituted cyclics which are the less desirable components of lubricating oils. Prior to adsorptive-separation, the lube oil stock is subjected to hydrogenation to saturate the aromatic and olefinic hydrocarbons (Column 4, Lines 14–30) to provide the more desirable paraffinic and naphthenic components of the lubricaring oil. The hydrogenative pretreatment is apparently conducted in a liquid-phase operation (Column 7, Lines 17–49). Since the charge stock, being an unrefined lube oil consisting of hydrocarbons in the $C_{18}$ to $C_{25}$ range, as distinguished from naphtha boiling range hydrocarbons, liquid-phase hydrogenation constitutes a judicious operating technique. Noteworthy, however, is the absence (1) of such hydrogenation technique in an isomerization/adsorption combination process and, more significantly, (2) liquid-phase conditions which prevent the saturation of aromatic nuclei.

U.S. Pat. No. 3,239,455 (Cl. 208-212), issued Mar. 8, 1966, is primarily concerned with the recovery of normal aliphatic hydrocarbons boiling in the kerosene boiling range for ultimate use in detergent manufacture (Column 1, Lines 14–45). Hydrogenation of the fresh feed charge stock is effected to eliminate nitrogenous and sulfurous compounds, and to saturate olefinic and aromatic hydrocarbons (Column 2, Lines 1–45). The hydrogenation pretreatment is effected in liquid phase (Column 6, Lines 43–54 and Column 12, Lines 20–25). As above indicated, the hydrotreating reaction employed in our combination aromatic isomerization/adsorption-separation process is effected at conditions which preclude aromatic hydrocarbon saturation.

SUMMARY OF INVENTION

As hereinbefore set forth, the process encompassed by our inventive concept is adaptable to the production and recovery of aromatic hydrocarbons from a mixture thereof with other aromatic hydrocarbons. In particular, our invention is intended for (1) the production and recovery of para-xylene from a mixture of other $C_8$-aromatic hydrocarbons and, (2) the production and recovery of para-cymene from a mixture of other $C_{10}$-aromatic hydrocarbons. In the interest of brevity and simplicity, the following discussion will be limited to para-xylene recovery and production.

The charge stock to the present combination process may be a substantially-pure $C_8$-aromatic mixture, or a mixture thereof with other hydrocarbons in the effluent from one or more petroleum refining processes. Examples of the latter include naphtha pyrolysis for ethylene production, which results in a considerable quantity of aromatics, and the well-known catalytic reforming process which is utilized principally to upgrade the motor fuel quality of naphtha boiling range hydrocarbons. Aromatic concentrates, benzene through $C_{10}$-aromatics, are often recovered by way of a liquid-liquid extraction technique using an organic solvent — e.g. a sulfolane-type compound, polyethylene glycol, etc. — to selectively absorb the aromatics and reject paraffins and naphthenes as a raffinate stream. Regardless, it is understood that the present process does not require the fresh feed charge stock to be a concentrated aromatic stream.

Considering $C_8$-aromatic concentrates, which will contain $C_7$-hydrocarbons (including aromatics) as well as $C_9$-plus hydrocarbons, they will generally be obtained from a hydrocarbonaceous stream which has previously been hydrotreated. For example, commonly practiced techniques dictate the hydrorefining of naphtha boiling range material, for olefinic saturation and the destructive removal of sulfurous and nitrogenous compounds, prior to its use as the feedstock for catalytic reforming. The aromatic concentrate recovered from the reformed product effluent will, therefore, be substantially free from these contaminating influences. Where such an aromatic concentrate is virtually immediately charged to the present process, it may be directly introduced into the adsorption-separation zone. However, we have also found that the concentrate requires hydrotreating where it has been in storage for a prolonged period prior to its use herein. In this situation, the aromatic concentrate is admixed with the effluent from the aromatic isomerization zone and introduced therewith into the hydrotreating zone.

Hydrotreating is effected after the aromatic isomerization reaction zone and prior to the adsorption-separation zone. Briefly, the $C_8$-aromatic charge stock, a concentrate for illustration purposes, is introduced into a so-called rerun column from which lower boiling components are removed as an overhead stream and $C_9$-plus material is withdrawn as a bottoms stream. The $C_8$-aromatics are separately recovered as a heart-cut and introduced into the adsorption-separation zone, contacting therein a crystalline aluminosilicate from the group of type X and type Y zeolites. Para-xylene is selectively retained within the sieves, and removed and recovered therefrom through the use of a suitable desorbent such as toluene. A para-xylene deficient concentrate of meta-xylene, ortho-xylene and ethylbenzene is withdrawn as a raffinate stream and introduced into an aromatic hydrocarbon isomerization reaction zone. Conversion to the para-xylene isomer is effected in contact with an acidic catalytic composite comprising a Group VIII noble metal component. The isomerized product effluent is subjected to separation to provide a hydrogen recycle stream and to remove the greater proportion of heptane and lower boiling material. Details of both the zeolitic adsorption-separation zone and the aromatic isomerization reaction zone are separately discussed hereinbelow.

Although the isomerization product effluent has been separated to provide the hydrogen-rich recycle stream (containing normally gaseous hydrocarbons) and to remove heptane and lower boiling material, the normally liquid $C_8$-aromatic concentrate will have dissolved therein an otherwise insignificant quantity of olefinic hydrocarbons. However, since the intent is to introduce this material into the molecular sieve adsorption-separation zone for recovery of the additional para-xylene, the minor amount of olefins must be removed in order to preserve the integrity of the crystalline aluminosilicate adsorbent. Accomplishment is effected via low-severity, liquid-phase hydrogenation which saturates the olefins without destroying the character of aromatic nuclei.

The $C_8$-aromatic concentrate is introduced into the upper section of a hydrogen saturation zone which is maintained at a pressure in the range of about 10 to about 500 psig., preferably from 10 to about 50 psig., and a temperature of about 100° F. to about 400° F. Precise conditions are selected to absorb a slight excess of hydrogen above that required to saturate the olefinic hydrocarbons. Hydrogen is most conveniently introduced into the saturation zone on pressure control — as the pressure decreases in the saturation vessel, the hydrogen rate is increased. The $C_8$-aromatic concentrate, containing sufficient dissolved hydrogen, is passed into the hydrotreating zone which has disposed therein a substantially non-acidic catalytic composite comprising a Group VIII noble metal component. Suitable noble metal components are ruthenium, osmium, rhodium, iridium, platinum, palladium and mixtures thereof. Preferably, these are composited with an alumina carrier material. Hydrotreating is carried out at low-severity conditions which results in a liquid-phase operation with respect to the $C_8$-aromatic hydrocarbons. These include temperatures of 100° F. to 400° F. and pressures from about 10 to about 500 psig. Through the use of the noble metal/alumina composite, the olefins will be saturated while the aromatic hydrocarbons will pass through virtually unscathed. The use of the term "non-acidic" is intended to allude to the fact that intentional steps to provide an acid function — e.g. incorporation of a silica or halogen component — in the catalyst, are not taken. Noble metals, especially platinum and palladium, as well as the alumina carrier material, possess sufficient natural acidity to effect hydrogenation reactions at a low severity operation. Concentrations of the noble metal component will be within the range of about 0.1% to about 1.5% by weight, calculated on the basis of the elemental metal. Relatively high liquid hourly space velocities of from about 2.5 to about 10.0 also contribute to the low severity operation by which there is no substantial aromatic hydrogenation.

The olefin-free $C_8$-aromatic concentrate from the hydrotreating zone is admixed with olefin-free fresh feed charge stock and introduced therewith into the rerun column, from which the $C_8$-aromatic feed to the adsorption-separation zone is recovered as a heart-cut. Where analyses indicate that the stored charge stock contains oxygenated and/or olefinic hydrocarbons, the same will be admixed with the effluent from the isomerization reaction zone and introduced therewith into the hydrogen saturation chamber. Where it becomes desirable to recover an ortho-xylene concentrate as a separate product stream, the rerun column will be maintained at conditions such that ortho-xylene is withdrawn with the $C_9$-aromatics as the bottoms stream; a second distillation column is subsequently used to recover ortho-xylene as an overhead product and $C_9$-aromatics as a bottoms stream.

ADSORPTION-SEPARATION

In describing the aromatic adsorption-separation section of the present combination process, particularly as directed toward selective para-xylene adsorption, it is understood that the precise manner by which the separation is effected forms no essential feature of our invention. Recognized is the fact that the prior art, whether published literature, or issued patents, abounds with various aspects of molecular sieve technology, and especially as applied to the adsorptive separation of various hydrocarbon mixtures. In such prior art, the terms "zeolite", "crystalline aluminosilicate" and "molecular sieve" are employed synonymously to allude to various structures of crystalline alumina and silica having pores in which one or more components of a given hydrocarbon mixture are selectively sorbed and retained within the pores, while one or more other components are rejected. Zeolitic adsorbents fall into a variety of classifications, generally determined by pore size and structure, depending upon the character of the component to be retained as well as the character of those components to be rejected. Thus, molecular sieves having a pore diameter of about 5 angstrom units are widely utilized to separate normal paraffins (sorbed and retained) from isoparaffins (rejected). Although the adsorption-separation may be effective using multiple fixed-bed zeolitic zones in swing-bed fashion, as illustrated in U.S. Pat. No. 2,920,037 (Cl. 208-310), issued Jan. 5, 1960, the more recent sophisticated simulated moving bed technique, as illustrated in U.S. Pat. No. 2,985,589, issued May 23, 1961, is preferred. These simulated moving bed processes utilize a multi-port rotary valve which may be of the type shown in U.S. Pat. No. 3,040,777 (Cl. 137-625.15), issued June 26, 1962.

With respect to the separation and recovery of para-xylene, suitable adsorbents are the type X and type Y crystalline aluminosilicate zeolites. General details of the compositions and manufacturing techniques of these may be had upon reference to U.S. Pat. No. 2,822,244 (Cl. 252-455), issued Apr. 14, 1959, and U.S. Pat. No. 3,130,007 (Cl. 23-113), issued Apr. 21, 1964, respectively. These molecular sieve zeolites contain exchangeable cationic sites which, by way of ion-exchange, will be prepared to contain one or more metal cations from the group of lithium, potassium, beryllium, magnesium, calcium, strontium, barium, nickel, copper, silver, manganese and cadmium. Generally, the cations of the metals from Groups I-A and II-A are preferred; a type X or type Y zeolite containing both potassium and barium is especially preferred.

Both liquid-phase and vapor-phase adsorptions may be utilized in this section of the present process, with the former being preferred. Liquid phase requires somewhat lower temperature levels which enhance the selectivity of the zeolite with respect to para-xylene. Typical adsorption-separation conditions include temperatures of from about 100° F. to about 400° F. and pressures in the range of from atmospheric to about 500 psig. Suitable desorbents constitute those materials readily separable from the $C_8$-aromatic components — i.e. having a different boiling range such that fractional distillation is feasible. Suitable desorbents include benzene, toluene, ethers, alcohols and ketones. Desorption conditions include the same ranges of temperature and pressure employed in the adsorption step. Additional details of the use of crystalline aluminosilicates in the adsorption-separation and recovery of para-xylene, may be obtained by reference to the following U.S. Pat. Nos.: 3,558,732 (Cl. 260-674), issued Jan. 26, 1971; 3,626,020 (Cl. 260-674 SA), issued Dec. 7, 1971; 3,663,638 (Cl. 260-674SA), issued May 16, 1972; 3,665,046 (Cl. 260-674SA), issued May 23, 1972; and, 3,696,107 (Cl. 260-674SA).

AROMATIC ISOMERIZATION

As previously stated in the discussion of the aromatic hydrocarbon separation section via zeolitic adsorption, it is acknowledged that the published literature is replete with illustrations of aromatic isomerization processes. The raffinate stream recovered from the separation zone contains principally ortho-xylene, meta-xylene and ethylbenzene. The specific technique employed to isomerize at least a portion of this mixture to produce additional para-xylene isomer is not a feature essential to the present invention. Preferably, the raffinate stream is contacted with an acidic catalytic composite, comprising a Group VIII noble metal component, in a hydrogen atmosphere. Suitable catalysts contain at least one metal from the group of ruthenium, rhodium, palladium, osmium, iridium, platinum and mixtures thereof, with platinum and/or palladium being particularly advantageous. As stated in U.S. Pat. No. 3,078,318 (Cl. 260-668), issued Feb. 19, 1963, the catalytically active metallic component are composited with an alumina carrier material, containing about 0.1% to about 8.0% by weight of combined chlorine and/or fluorine; the noble metal concentration will be in the range of about 0.01% to about 1.0% by weight, calculated as the elemental metal.

With this type of catalytic composite, the para-xylene deficient raffinate will be isomerized to produce additional para-xylene at operating conditions including temperatures of from 700° F. to about 1100° F., preferably 750° F. to 1000° F., and pressures in the range of about atmospheric to about 1,500 psig., preferably 100 to 700 psig. The reactions are effected in the presence of hydrogen in an amount of about 1.0 to about 10.0 moles per mole of hydrocarbon charge. Raffinate components will be charged to the isomerization reaction zone at a weight hourly space velocity of from 0.5 to about 10.0, preferably in the range of about 1.0 to about 5.0. Particular operating conditions will be dependent upon the particular mixture of $C_8$-hydrocarbons in the feedstock; however, combinations of higher pressures and lower temperatures should be avoided to assure substantially no aromatic hydrogenation.

Additional details of suitable aromatic isomerization techniques may be had upon reference to the following U.S. Pat. Nos.: 3,409,685 (Cl. 260-668), issued Nov. 5, 1968, wherein isomerization is effected with a Group VIII metal component on an alumina matrix having crystalline aluminosilicate suspended therein, and in the presence of a sulfur-containing promoter; 3,409,686 (Cl. 260-668), issued Nov. 5, 1968, wherein the catalyst is platinum on an alumina carrier having finely-divided zeolitic material suspended therein; and, 3,637,881 (260-668A), issued Jan. 25, 1972, which teaches the suppression of transalkylation through the addition of a basic nitrogen-containing compound to the isomerization reaction zone.

BRIEF DESCRIPTION OF DRAWING

Various embodiments of the combination process encompassed by our inventive concept are presented in the accompanying drawing. These are presented by way of a simplified schematic flow diagram in which miscellaneous appurtenances such as pumps and compressors, heaters and coolers, condensers, heat-exchangers and heat-recovery circuits, start-up lines, valving and similar hardware have been omitted. These are not essential to an understanding of the process, and the utilization thereof, to modify the illustration, is well within the purview of one possessing the requisite skill in the petroleum processing field of endeavor. Certainly the resulting modification will not be beyond the scope and spirit of the appended claims.

DETAILED DESCRIPTION OF DRAWING

The charge stock, being the deheptanized portion of the effluent from a catalytic reforming process — i.e. $C_8$-hydrocarbons to 400° F. end boiling point — is introduced into the process via conduit 1. Should an alternative feedstock such as deheptanized hydrotreated pyrolysis gasoline be charged, there is no need to divert the same via line 2 into hydrogen saturation zone 19. The hydrotreated, catalytically-reformed liquid effluent is admixed with a previously hydrotreated effluent in line 3, the mixture continuing therethrough into rerun column 4. This column serves to remove trace amounts of heptanes and lower-boiling hydrocarbons, as well as normally vaporous material as an overhead stream in line 5.

Normally liquid hydrocarbons containing nine or more carbon atoms per molecule are recovered by way of conduit 6. In many instances, the recovery of an ortho-xylene product will be desirable, and rerun column 4 will be maintained at conditions of temperature and pressure such that ortho-xylene is withdrawn with the C$_9$-plus hydrocarbons in line 6, to be separated therefrom as an overhead stream in another fractionation column not illustrated. The C$_8$-aromatic concentrate is recovered from column 4 as a heart-cut in line 7, and is introduced thereby into aromatic separation zone 8. On a weight basis, this C$_8$-aromatic concentrate contains about 17.8% ethylbenzene, 17.8% para-xylene, 42.7% meta-xylene and 21.7% ortho-xylene.

Aromatic separation zone 8 contains an adsorbent of type X structured zeolitic material loaded with about 1.3% sodium, 3.5% potassium and 18.6% barium, on a weight basis. Both adsorption and desorption operations are effected at liquid-phase conditions of 350° F. and about 140 psig. Para-xylene is adsorbed by the molecular sieves, and the material not selectively retained is removed by way of line 10. The adsorbent is contacted with a desorbent — e.g. toluene, diethylbenzene, etc. — to displace the selectively adsorbed para-xylene which is recovered via conduit 9. The para-xylene deficient stream in line 10 is introduced thereby into aromatic isomerization zone 12 in admixture with a hydrogen-rich vaporous phase in line 11. Employed herein is a catalytic composite of alumina containing about 0.375% by weight of palladium and about 1.9% by weight of fluorine. Operating conditions include a pressure of about 175 psig., a temperature of 750° F., a liquid hourly space velocity of about 2.0 and a hydrogen to hydrocarbon mole ratio of about 6.0:1.0. The isomerized effluent is passed into high-pressure separator 14 by way of line 13 at a temperature of about 90° F. Excess hydrogen-rich vapors, not recycled to isomerization zone 12 are vented under pressure control (not illustrated).

Normally liquid hydrocarbons, containing dissolved normally vaporous material and olefinic hydrocarbons are withdrawn from separator 14 through line 15, and introduced thereby into deheptanizer 16. Heptane and lower boiling hydrocarbons, including vaporous material, are recovered through line 17, while the C$_8$-aromatic concentrate is recovered by way of conduit 18. As above stated, where the fresh feed in line 1 contains olefinic hydrocarbons, or other zeolite contaminating influences, it will be mixed with the aromatic concentrate in line 18 and introduced therewith into hydrogen saturation zone 19.

Hydrogen saturation zone 19 contains a plurality of trays or other devices creating intimate mixing of the hydrocarbons in line 18 and the hydrogen in line 20. With respect to the latter, a portion thereof may be supplied from the excess hydrogen-rich stream not recycled to aromatic isomerization zone 12 via line 11. Saturation with hydrogen is effected at a temperature of about 360° F. and a pressure of about 35 psig. The absorbed hydrogen-containing C$_8$-aromatic concentrate is withdrawn through line 21 and introduced into hydrotreating zone 22. Therein the mixture contacts a non-acidic catalytic composite of about 0.375% by weight of platinum combined with an alumina carrier material. The liquid hourly space velocity is about 3.0, while the temperature and pressure are essentially the same as those employed in the aromatic separation zone — 350° F. and 140 psig. Olefin-free C$_8$-aromatics are withdrawn via line 3 and introduced into rerun column 4 in admixture with the fresh feed charge stock in line 1.

The foregoing specification, particularly when read in conjunction with the accompanying drawing, clearly indicates the method by which the present combination process is effected.

We claim as our invention:

1. A process for the production and recovery of para-xylene from a mixture of C$_8$-aromatic hydrocarbons, which process comprises the sequential steps of:
   (a) contacting said mixture with a crystalline aluminosilicate adsorbent, in an adsorption-separation zone, at conditions selected to effect the selective retention therein of para-xylene;
   (b) withdrawing a para-xylene deficient C$_8$-aromatic raffinate stream from said adsorption-separation zone and contacting said adsorbent with a desorbent to effect removal and recovery of para-xylene therefrom;
   (c) introducing said raffinate stream into an aromatic isomerization reaction zone maintained at isomerization conditions which convert C$_8$-aromatic hydrocarbons into para-xylene and which effect the production of olefinic hydrocarbons;
   (d) hydrotreating the resulting isomerization reaction zone effluent, in a hydrotreating zone, at hydrotreating conditions selected to (i) provide a liquid-phase operation and (ii) saturate said olefinic hydrocarbons without substantial saturation of C$_8$-aromatic hydrocarbons; and,
   (e) introducing at least a portion of the resulting olefin-free reaction zone effluent into said adsorption-separation zone to recover additional para-xylene.

2. The process of claim 1 further characterized in that said C$_8$-aromatic hydrocarbon mixture is combined with said olefin-free effluent and introduced therewith into said adsorption-separation zone.

3. The process of claim 1 further characterized in that said C$_8$-aromatic hydrocarbon mixture is combined with said isomerization reaction zone effluent and introduced therewith into said hydrotreating zone.

4. The process of claim 1 further characterized in that said C$_8$-aromatic hydrocarbon mixture comprises para-xylene and at least one aromatic hydrocarbon from the group of meta-xylene, ortho-xylene and ethylbenzene.

5. The process of claim 1 further characterized in that said hydrotreating conditions include a temperature in the range of about 100° F. to about 400° F. and a pressure from about 10 to about 500 psig.

6. The process of claim 5 further characterized in that said hydrotreating conditions include a pressure in the range of about 10 to about 50 psig.

7. The process of claim 1 further characterized in that said adsorbent is selected from the group consisting of type X and type Y structured zeolites.

8. The process of claim 1 further characterized in that said desorbent comprises diethylbenzene.

9. The process of claim 1 further characterized in that said aromatic isomerization reaction zone has disposed therein a catalytic composite comprising a Group VIII noble metal component.

10. The process of claim 1 further characterized in that said hydrotreating reaction zone has disposed therein a substantially non-acidic catalytic composite comprising a Group VIII Metallic component.

* * * * *